US006902657B2

(12) United States Patent
Minarik et al.

(10) Patent No.: US 6,902,657 B2
(45) Date of Patent: Jun. 7, 2005

(54) ELECTROPHORESIS SEPARATION MEDIA AND METHODS

(75) Inventors: Marek Minarik, Sunnyvale, CA (US); Melanie M. Mahtani, Portola Valley, CA (US)

(73) Assignee: Amersham Biosciences Corp., Piscataway, NJ (US)

( * ) Notice: Subject to any disclaimer, the term of this patent is extended or adjusted under 35 U.S.C. 154(b) by 569 days.

(21) Appl. No.: 09/882,523

(22) Filed: Jun. 15, 2001

(65) Prior Publication Data

US 2002/0189948 A1 Dec. 19, 2002

(51) Int. Cl.[7] .............................................. B01D 57/02
(52) U.S. Cl. ...................................... 204/451; 204/454
(58) Field of Search ................................. 204/451, 454

(56) References Cited

U.S. PATENT DOCUMENTS

| | | | | |
|---|---|---|---|---|
| 4,865,706 A | | 9/1989 | Karger et al. ............ 204/182.8 |
| 5,089,111 A | * | 2/1992 | Zhu et al. .................... 204/451 |
| 5,370,777 A | | 12/1994 | Guttman et al. ......... 204/182.8 |
| 5,374,527 A | | 12/1994 | Grossman ...................... 435/6 |
| 5,567,292 A | * | 10/1996 | Madabhushi et al. ....... 204/451 |
| 6,156,178 A | | 12/2000 | Mansfield et al. .......... 204/457 |

FOREIGN PATENT DOCUMENTS

WO    WO 99/22228    5/1999

OTHER PUBLICATIONS

Barry et al., "Analysis of modified oligonucleotides by capillary electrophoresis in a polyvinylpyrrolodone matrix coupled with electrospray mass spectrometry". J. of Chromatography A, 732, 159–166(1996).*

J. Noolandi, "A New Concept for Separating Nucleic Acids by Electrophoresis in Solution Using Hybrid Synthetic End Labelled–Nucleic Acid Molecules", *Electrophoresis*, 1993, 14, pp. 680–681.

W. Schutzner et al., "Separation of Diastereomeric Derivatives of Enantiomers by Capillary Zone Electrophoresis With a Polymer Network: Use of Polyvinylpyrrolidone as Buffer Additive", *J. Chromatography*, 1993, 639, pp. 375–378.

P. Blatny et al., "Linear Polymers Applied as Pseudo–Phases in Capillary Zone Electrophoresis of AZO Compounds Used as Textile Dyes", *J. Chromatography*, 1995, 717, pp. 157–166.

J. P. Barry et al., "Analysis of Modified Oligonucleotides by Capillary Electrophoresis in a Polyvinylpyrrolidone Matrix Coupled with Electrospray Mass Spectrometry", *J. Chromatography*, 1996, 732, pp. 159–166.

P. Mayer et al., "Theory of DNA Sequencing Using Free–Solution Electrophoresis of Protein–DNA Complexes", *Anal. Chemistry*, 1994, 66, pp. 1777–1780.

J. Sudor et al., "End–Label, Free–Solution Capillary Electrophoresis of Highly Charged Oligosaccharides", *Anal. Chemistry*, 1995, 67, pp. 4205–4209.

Christine Piggee et al., "Capillary electrophoresis for the detection of known point mutations by single–nucleotide primer extension and laser–induced fluorescence detection", *Journal of Chromatography A*, vol. 781, 1997, pp. 367–375.

* cited by examiner

Primary Examiner—Ling-Sui Choi
(74) Attorney, Agent, or Firm—Schneck & Schneck; Thomas Schneck; David M. Schneck

(57) ABSTRACT

A low molecular weight non-entangled polyvinylpyrrolidone for use as a separation media for microchannel electrophoretic separation. The separation media may be used in a system in which multiple samples of small compounds are injected into a single microchannel at time spaced intervals followed by a continuous detection interval.

16 Claims, 3 Drawing Sheets

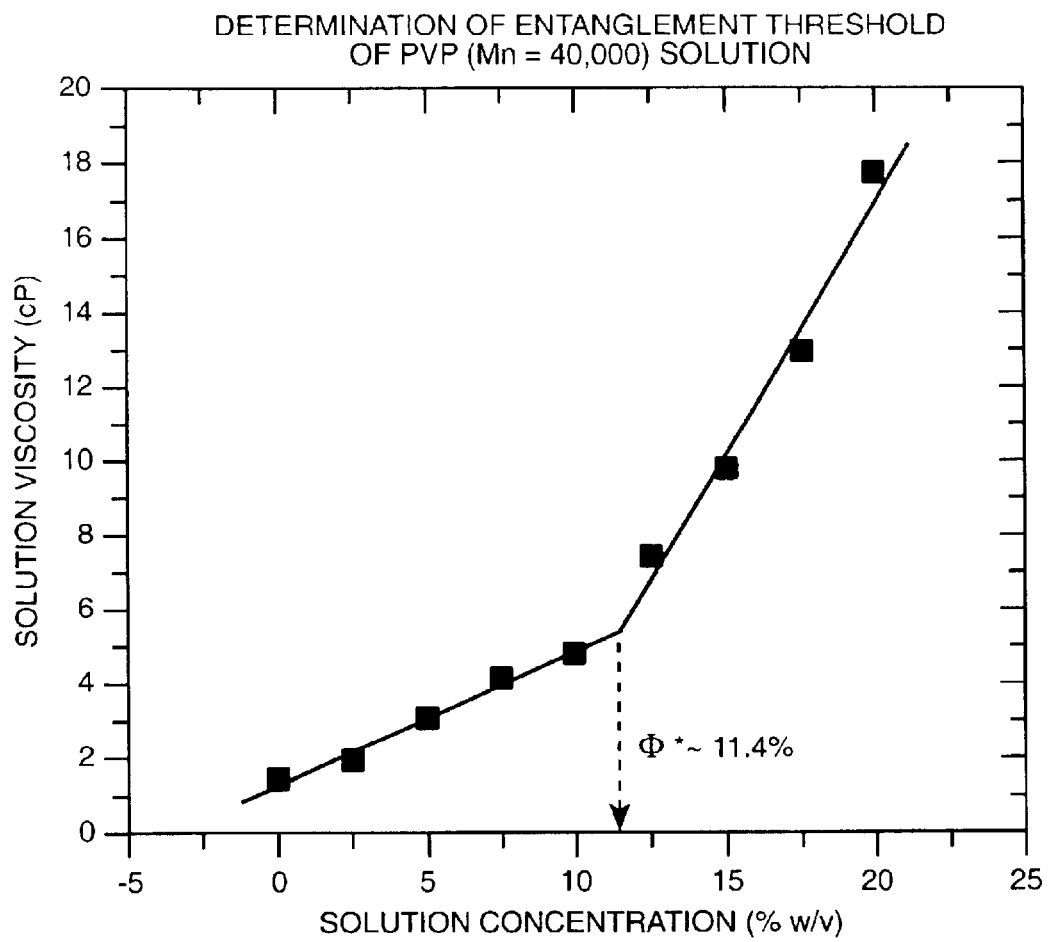
FIG._1A
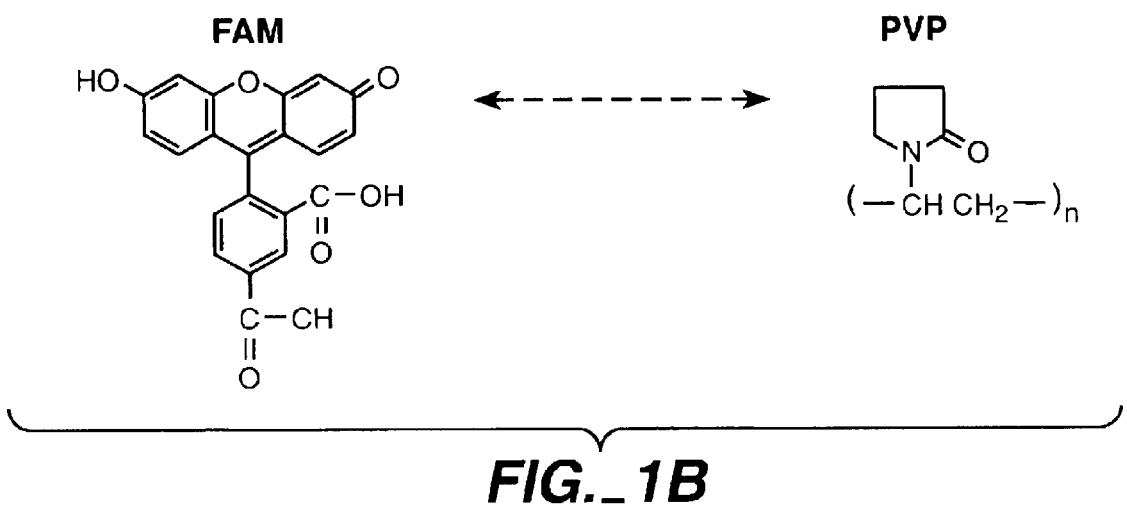
FIG._1B

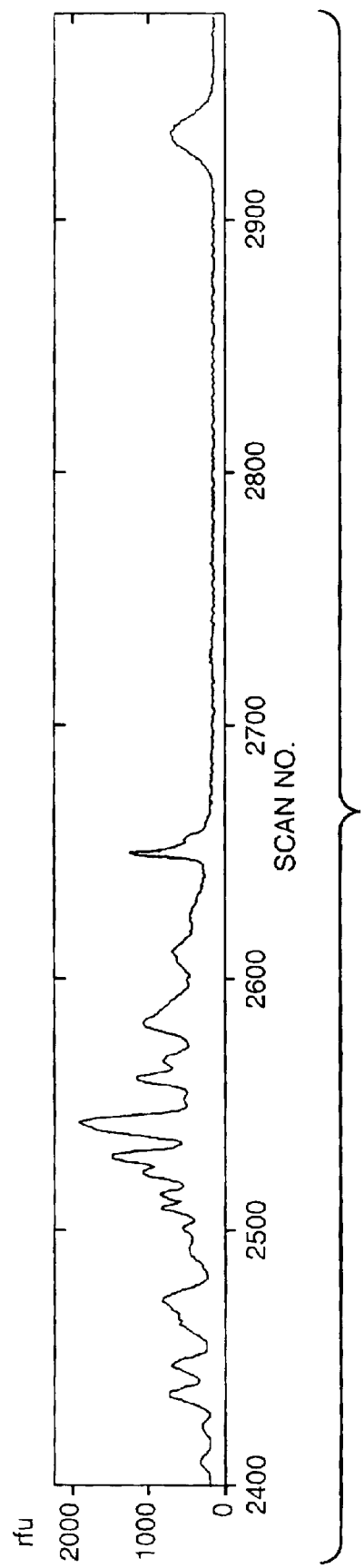
FIG._2A
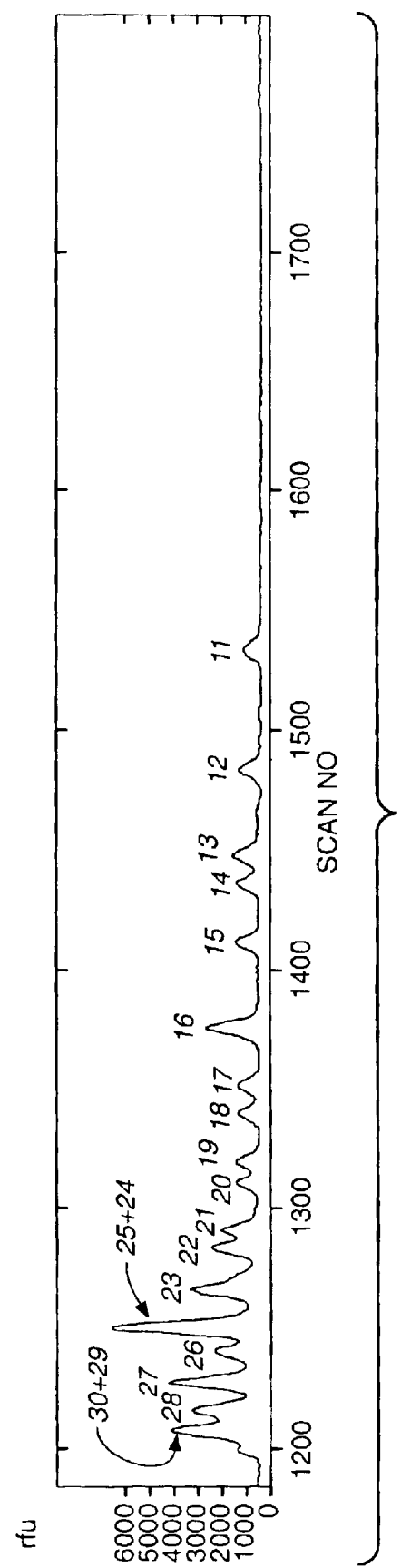
FIG._2B

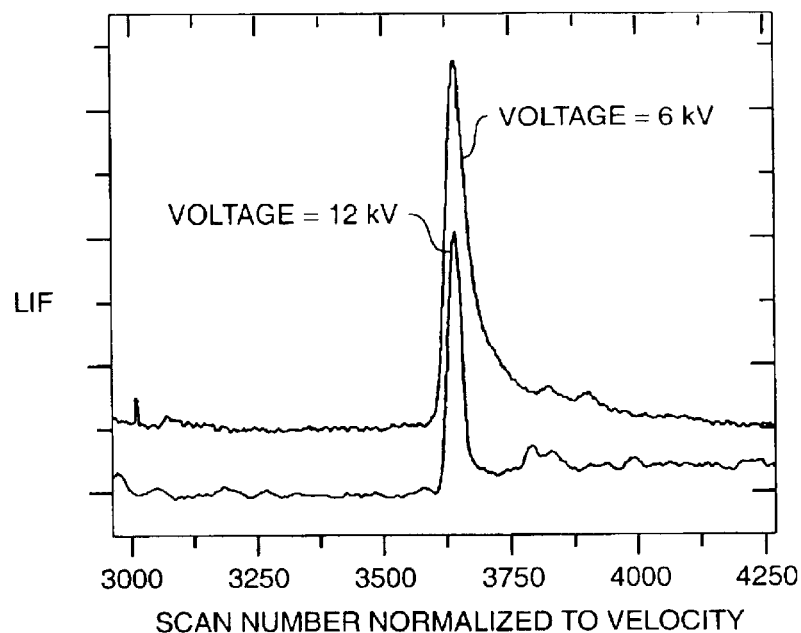
FIG._3A
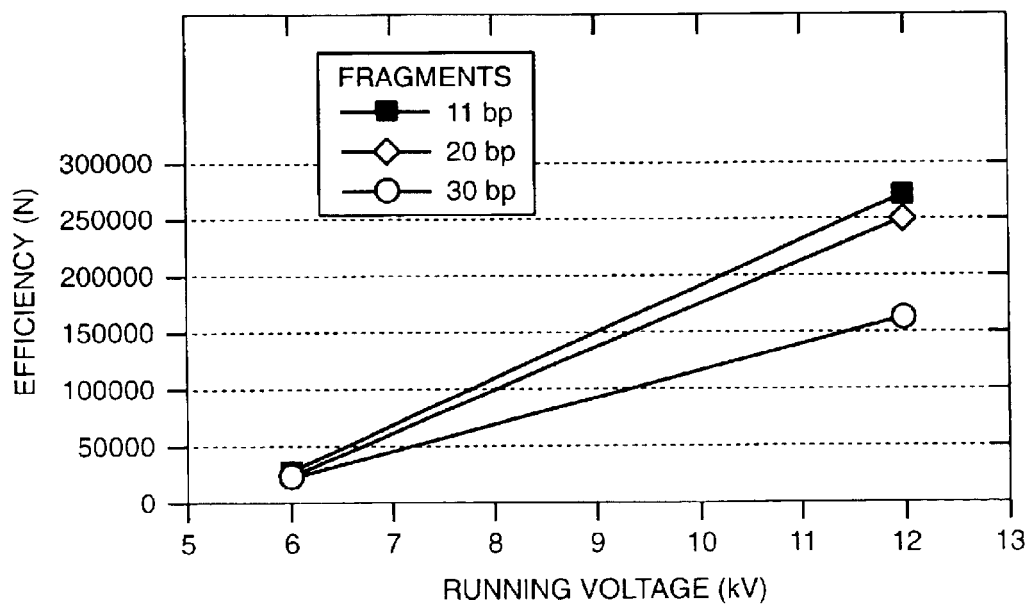
FIG._3B

ELECTROPHORESIS SEPARATION MEDIA AND METHODS

TECHNICAL FIELD

The present invention relates generally to electrophoretic separation and analysis of compounds and more specifically to media for the separation of compounds.

BACKGROUND OF THE INVENTION

The analysis of biological and other compounds often begins with the separation of macromolecules. Capillary electrophoresis has proved a valuable tool for the separation of macromolecules, allowing their further analysis or isolation. Compounds may be separated by size, charge, affinity to complexing agents etc.

Capillary electrophoresis systems present various advantages. First, the low sample volume consumption required for capillary electrophoretic separation reduces costs for sample analysis. Second, the high surface to volume ratio, characteristic of a capillary dimension microchannels, allows for efficient heat dissipation. The resulting lower joule heating of the capillary allows greater voltage to be used in separations. Using higher voltages makes the separation more rapid, mitigating against diffusion from band-spreading. Third, capillary electrophoresis systems are readily adaptable to high throughput sample processing. With rapid increase in genomic information, the need for the rapid analysis of nucleic and samples is increasingly acute. Capillary electrophoresis systems are readily adaptable to multiplexing to increase sample throughput. Capillary dimension microchannels may be designed as an array of microchannels, such as a group of capillary tubes in a capillary array electrophoresis system (CAE system) or as a plurality of lanes on an electrophoresis chip. In addition, the use of multiple detectable labels that may be separately detected by a detector allow a second level of multiplexing, further increasing throughput. Finally, various configurations of sample pooling allow another level of multiplexing.

Capillary electrophoresis requires a microchannel (generally of capillary tube dimensions) that is filled with a separation media. The sample is introduced at one end of the microchannel and after migration through the length of the channel is detected at the opposite end. The separation media contains an electrolyte buffer allowing the current to flow from an anode to a cathode. In one common method of capillary electrophoresis, a polymer included in the separation medium acts as a sieve for the separation of biomolecules. The movement of the biomolecules is inhibited by the sieving matrix, with smaller molecules able to overcome the friction and to move more quickly through the matrix than larger molecules.

U.S. Pat. No. 4,865,706 discloses the use of crosslinked polyacrylamide gel as a molecular sieving agent for the separation of charged molecules. The interior wall of the capillary is covalently modified with a bonding agent. Typically, polymerization of a crosslinked separation matrix takes place inside the capillary tube. The mixture of monomer and a cross-linker is injected into the capillary and catalytically converted to a polymerized form. This may result in incomplete polymerization formation of bubbles and lack of gel uniformity, issues which represent the main drawback of the cross-linked separation matrices. Another drawback is the difficulty in removing the crosslinked gel.

U.S. Pat. Nos. 5,089,111; 5,374,527 and 5,370,777 describe a significant improvement in CE matrix technology by replaceable matrix composed of an entangled solution of linear polymer. Although less rigid than crosslinked gel, the network of dynamic pores in entangled matrix provides equivalent media for separation of biomolecules. The main advantage of the entangled polymer media is the preparation outside the capillary resulting in a high homogeneity of the matrix. Another significant advantage is the ability to replace the matrix in capillaries after each run using a high pressure, thus increasing the run to run reproducibility.

Various polymers have been proposed as entangled media for the separation of charged biomolecules. U.S. Pat. No. 5,567,292 proposes the use of a polymer for both suppression of electroosmotic flow and as a matrix for separation of polynucleotides in the size gauge of about 100 to 500 nucleotides in an uncoated capillary. The separation compound would be water-soluble, lack charged groups in a liquid media of 6–9 pH, have a molecular weight of $5 \times 10^3$ to $1 \times 10^6$ daltons and concentration between 0.001 and 10%. These separation media include polylactams, such as polyvinylpyrrolidone, as well as substituted polyacrylamide derivatives.

With these types of media entanglement is a prerequisite for an efficient separation of oligonucleotides in the gauge from approximately 100 to 1000 bases in length.

The viscosity of an entangled medium requires high-pressure introduction into the capillary. In addition, newly developed CE methods utilizing multiple electrokinetic injections of samples are not compatible with classic entangled matrices. The multiple sample loads as well as interruption in the current required in multiple injections is believed to degrade the entangled matrix. A primary feature of an entangled matrix is the high sieving capacity attendant with the relatively high molecular weight of the sieving polymers. However, this feature is not required for the separation of short oligonucleotides. Assays for SNP typing; such as single-nucleotide primer extension (SnuPE) or oligonucleotide ligase assay (OLA); produce short oligonucleotide fragments (100 bases or smaller). To avoid the requirement of high pressure fill and matrix inhomogeneity due to the sample impact, an alternative separation media that provides high separation speed and resolution of small oligonucleotide fragments is desired.

In 1993, a modification of free-zone CE used for separation of small ionic compounds was developed. In this method, dilute linear polymers are added to the CE buffer electrolyte. These polymeric additives act as pseudo-phases for separation. In contrast to sieving, pseudo-phase leads to separation of sample mixture through hydrogen bonding, hydrophobic interactions, steric interactions, and dipole-dipole interactions. However, to date the use of these polymers for pseudo-phase separation has been fairly limited. In one example a high-molecular weight polyvinylpyrrolidone [PVP] was used at low concentration as a buffer additive for the capillary electrophoresis separation of diastereomeric derivatives of tryptophan. Schutzner, et al., J. Chromatogr. 639 (1993) 375–378. In a similar manner, a combination of polyethylene glycol and polyvinylpyrrolidone were used for the electrophoretic separation of azo dye compounds based on their inherent hydrophobicity. Blatny et al., J. Chromatogr. 717 (1995) 157–166. Similar high-molecular PVP matrix was applied for separation of nucleotide adducts (Barry et al.). These studies provided an initial indication that PVP could be used as a pseudophase for the separation of hydrophobically modified oligomers.

One of the most frequently used detection techniques in CE is laser-induced fluorescence. Because DNA molecules exhibit no native fluorescence, synthetic dyes are commonly introduced at the 5'-end of each DNA molecule. Most fluorescent dyes include aromatic rings, capable of excitation of PI-electrons and subsequent emission of fluorescence light. By nature, the aromatic rings exhibit inherent hydrophobicity, which can be directly utilized for interaction with PVP pseudophase matrix leading to chromatography-like separation.

It is an object of the invention to provide a separation matrix and attendant method for using the separation matrix, which is able to provide high resolution of short fluorescently labeled oligonucleotide fragments (10–100 base fragments).

It is a further object to provide a lower viscosity separation media. Such a media could be introduced into a capillary with low-pressure nitrogen filling.

It is a further object of the invention to provide a separation media that does not require a complex polymerization and does not exhibit entanglement property such as sieving. It is a further object to provide a separation procedure for short oligonucleotide fragments that shows superior peak spacing (indicating separation selectivity) and peak efficiency.

It is a further object to allow the use of higher voltages than are allowed with the use of a separation media containing an entangled polymer matrix.

It is a further object to provide a CE media that may be used for a multiple injection procedure for separation samples containing small compounds.

SUMMARY OF THE INVENTION

The above objects have been achieved through the use of a low molecular e.g. Mn<1000000 Da non-entangled polyvinylpyrrolidone for use as a separation media in microchannel electrophoretic preparation systems. This non-toxic medium provides a low cost tool for the separation of compounds with hydrophobic properties such as fluorescently labeled oligonucleotides. The low viscosity of a non-entangled separation media simplifies the filling of microchannels. The use of this separation media is especially useful for use in a system that enables multiple time spaced injections of multiple samples into a single capillary tube as the non-entangled medium is not affected by the sample migration and thus able to withstand multiple loads of sample mixture. The time spacing of the sample injection is sufficient such that each sample set is detectably separated when the samples reach the injector. This provides a method of high throughput sample analysis such as screening of single-nucleotide polymorphisms (SNPs), oligonucleotide quality control (QC) and other related oligonucleotide assays.

BRIEF DESCRIPTION OF THE DRAWINGS

FIG. 1A is a plot of the viscosity as a function of PVP concentration (PVP MN=40,000).

FIG. 1B is a chemical diagram of polyvinyl pyrrolidone and a fluorescent label (FAM).

FIG. 2A is an electropherogram of the separation of small oligonucleotide fragments using linear polyacrylamide as the separation media.

FIG. 2B is an electropherogram of the separation of the same compounds separated in FIG. 2A with non-entangled polyvinylpyrrolidone as the separation media.

FIG. 3A is an illustration of a peak shape using PVP as the separation media at 6 and 12 kV.

FIG. 3B is a graph of an increase in peak efficiency as running voltage increases obtained for three oligonucleotide fragments.

DETAILED DESCRIPTION OF THE INVENTION

In CE, high molecular weight polyvinylpyrrolidone (Mw≧1,000,000) has been used as an entangled matrix for the separation of DNA fragments. The separation mechanism was based on sieving principle enzymatic preferential to large fragments generated by reactions in DNA sequencing or microsatellite genotyping. In the present invention the presence of fluorescent labels on short oligonucleotides (designed for their luminescence detection) is utilized for separation resulting from interactions with a solution of low molecular PVP (Mn<1,000,000 Da. The hydrofobic label represents the point of contact with the phase. For a small fragment the label constitutes more significant portion of size, therefore its migration will be influenced more significantly by the interaction. As a result, the separation mechanism is opposite to sieving with the larger compounds eluting first and the small compounds eluting last. The low molecular PVP allows for preparation of high concentrated, non-entangled low viscosity PVP solutions (up to 20% w/v) which exhibit higher number of interacting vinylpyrrolidone units per volume and significantly increase the separation power. This media is especially suitable for the separation of fragments 10–100 bases in length. The low viscosity of the separation media allows for the capillary to be filled and emptied under low pressure. Without the need for high pressure filling, the microchannel filling system does not need to be designed with high-pressure assembly.

The non-entangled PVP has the advantage of low viscosity. With reference to FIG. 1A, the solution viscosity is plotted as a function of PVP concentration. PVP Mn=40,000 was used in this example. The entanglement threshold $\Phi^*$ is defined as the point of change of the slope, representing a marked increase in solution viscosity. In the presented example, for PVP Mn=40,000 the $\Phi^*$ is at 11.4%. Above this concentration the viscosity shows a rapid increase. The $\Phi^*$ concentration will vary with the molecular weight of PVP and temperature. Generally the threshold $\Phi^*$ will be lower for high-molecular polymers resulting in their significant solution viscosity already at low concentrations.

As indicated in the background, a pseudophase separation assay does not require an entangled separation matrix. Instead, the compounds are separated based on chemical interactions with the separation media. Such interactions may be hydrophobic interactions, hydrogen bonding, or dipole-dipole interactions. In the present separation media, the small nucleic acid fragments are each labeled with at least one compound having multiple aromatic rings. These multiple aromatic rings are believed to interact with the cyclic amides present on the PVP molecules. This interaction slows the migrating nucleic acid molecules. For a larger nucleic acid molecule, a smaller percentage of the size of the molecule is composed of the label compound. In contrast, for smaller oligonucleotide fragments, a larger percentage of the molecule will be the label compound. As a result, the smaller fragments will be more likely to have their mobility affected upon interactions with the separation media, resulting in a longer elution times. In contrast, the larger fragments, having a smaller percentage of the molecule comprised of the label, will be less affected by PVP and have a relatively faster migration rate causing these fragments to be detected before the smaller fragments.

With reference to FIG. 1B, the structure of a fluorescent label, FAM, and of PVP monomer is shown. The multiple aromatic rings of FAM are believed to interact with the cyclic amide ring of the PVP molecule. This interaction slows the mobility of FAM-labeled DNA molecule migrating through a non-moving PVP media. In contrast to free zone electrophoresis, which separates molecule based on charge alone, this interaction between aromatic rings provides an additional mechanism for the separation of short oligonucleotide fragments.

Labels, such as FAM, may be conjugated to nucleotide bases using conjugation methods that are known in the art. Labeled nucleotides are also available from commercial sources such as Molecular Probes, Eugene Oreg. These bases may then be incorporated into DNA fragments during synthetic reactions. As noted, primer extension, rolling circle amplification, ligase assay, as well as other methods may be used in nucleic analysis and produce short DNA fragments. The production of short fragments facilitates further analysis.

Non-entangled PVP may be used in a variety of microchannel electrophoretic separation systems. The term "microchannel" and "capillary" are used interchangeably and broadly refer to an elongate channel in which electrophoresis may be carried out. The channel will have an internal cross section that may be circular, rectangular, square or have other dimensions. The channel may be in the interior bore of a tube or may be a channel or groove in a plate, chip, or other substrate. Such a channel may be fabricated by dicing, etching, cast molding, or other known manufacturing. Characteristic of all of these channels is a high surface to volume ratio of the surface in contact with the separation media, providing for efficient heat dissipation during electrophoretic separation procedures. It is preferred that the microchannel be made of silica, quartz, or other similar material. Heat dissipation is further enhanced by having the total material thickness of the material from which the microchannel be fabricated by as small as possible.

One system in which the present separation media may be useful is described in U.S. patent application Ser. No. 09/556,897, incorporated by reference for all purposes herein, describes a capillary electrophoresis chip and system for electrophoretic separation of charged compounds. This system includes a separation chip having a highly parallel set of microchannels on a substrate. Each microchannel has individual leads to allow for individual operation of each microchannel. The system also includes an automated system for moving samples from a sample plate to the individual openings of each microchannel. In this system, the PVP separation matrix could be included as the separation media. This media would provide a simplified loading and washing of the microchannels. If entangled separation matrices are used, the microchannels of the separation chip would be filled under pressure with pressure tight seals and the microchannels would be washed using a high-pressure wash system. When a non-entangled PVP separation matrix is used, the microchannels could be filled without using a high-pressure wash for the loading and washing of the microchannel.

U.S. Pat. No. 6,156,178, hereby incorporated for all purposes herein, illustrates an alternative system using microchannels, as well as a method of compound separation in which the present separation media is well suited. In this reference, a capillary array electrophoresis system is described. This system is currently sold as the MegaBACE® system from Molecular Dynamics, Sunnyvale, Calif. a division of Amersham Pharmacia Biotech, Piscataway, N.J. In this system, a highly parallel set of capillary tubes is arranged such that the set may be used for the parallel separation in 96 capillaries. In this system the capillary array is filled by high-pressure injection of an entangled separation matrix. Samples are electrokinetically injected into the capillaries and the ends of the capillaries are brought into contact with an anode reservoir and a cathode reservoir. Following a separation procedure, the media from the capillary may be removed and the capillary refilled with the separation media. If the media of the present invention were used in this system, the capillary could be filled using a low pressure filling method. In addition, cleaning of the capillary tubes would be simplified and would not require high pressure pumping to empty the contents of the capillary tube.

This reference also discloses a system and method for increasing the throughput of the analysis of small fragment samples. In this method, a first sample containing multiple small compounds to be separated is initially injected into the microchannel and exposed to an electrophoretic current for a selected interval. The current causes the sample to migrate away from the injection end of the capillary and towards a detection area on the microchannel at a location distal from the injection end. After a selected interval, a second sample containing multiple small fragments is injected into each capillary. The timing of the injections (i.e. the interval between each injection) is selected such that when the compounds reach the detection location on the microchannel (e.g. capillary) each injected set of compounds is detectably separated from any other set of compounds (i.e. there are no peak overlaps) and the compounds within each sample are detectably separated. This cycle of injections is repeated a number of times, with each sample injection followed by an interval of separation in which the compounds in the sample migrate away from the injection end and toward the detection location. When the first sample set is proximate to the detection location, all of the injected samples are continuously detected as each compound in a sample migrates past the detection location. Using this method of multiple injections, it is possible to greatly increase the throughput of analysis of short oligonucleotide fragments.

The PVP separation media, when used as a non-entangled pseudophase, should be more stable than linear polyacrylamide, making PVP a better media for multiple injection separation procedures. The homogeneity of an entangled matrix, such as entangled linear polyacrylamide is often affected by the impact of migrating compounds. This requires that the matrix be replaced after each separation procedure. In addition, the frequent voltage interruptions are likely to cause disruptions in matrix entanglement and may limit the total number of injection cycles possible with the entangled matrix. It is expected that a homogenous media consisting of low-molecular weight pseudophase separation polymer dissolved in buffer will be less susceptible to buffer interaction or frequent voltage interruptions. This would make PVP an ideal media for this procedure.

The use of PVP as the separation media would prove valuable for multiple injections. Generally, the samples that are best suited for multiple injections are samples comprised of small molecules. Samples containing labeled oligonucleotide fragments under 100 bases in length are well suited for multiple injection, with fragments from 10–30 bases in length best suited for such injection. The use of non-entangled PVP as the separation matrix provides a separation media that is specifically selected for use with these fragment sizes.

In either capillary array electrophoresis or in capillary chip electrophoresis a variety of detectors may be used to detect the compounds as the compounds migrate past a detection location. In many nucleic acid analysis systems, laser induced fluorescence (LIF) is detected by a confocal detector. The oligonucleotide fragments are labeled with an optically detectable label. As molecules migrate past the detection location, a laser illumination beam excites fluorescence from the label. This fluorescence is collected from a thin object plane within the capillary at the detection window and transmitted to a detector. One advantage of this method of optical detection is the ability of the detector to identify different labels based on the emission profile characteristic of the label. This provides an additional method of multiplexing, allowing simultaneous detection of labels having different fluorescent profiles.

In addition to LIF detection, other detection methods are adaptable for use with the present separation media. These include detection with mass spectrometry and electrical conductivity gating. Either of these detection methods allows detection of separated charged compounds. In either method, the charged compound being separated may be conjugated to a label having multiple aromatic rings. This would both aid in the pseudophase separation of the sample molecules and aid in detection using various detection methods.

In most electrophoretic separation methods some coating is used to mask the interior surface of the microchannel with a compound that is neutrally charged. This suppresses electroosmosis. Electroosmosis is the bulk flow of the separation media caused by interaction with the positively charged buffer ions and the negatively charged silica surface of the separation microchannel. The surface may be masked with dynamic coatings or covalent modification to form an interior surface coating. In one coating, a thin layer of polyacrylamide is polymerized to coat the interior of the microchannel with a highly viscous layer. In addition other coatings are known in the art. However, it is believed that uncoated capillaries may also be used. PVP is known to suppress electroosmosis. See Lido and Young, Anal. Chem. 70 (1998), p. 13. The capillary was filled using nitrogen gas pressure at 100 psi. In contrast, up to 1000 psi is required for current linear polyacrylamide filling of capillaries.

Although the present description of the invention has been limited to non-entangled PVP, any hydrophobic, non-entangled, soluble polymer may be the equivalent of PVP at a low molecular weight.

In the following example, the use of the non-entangled PVP matrix is illustrated.

Preparation of Separation Media

The separation media was prepared by dissolving 3.03 g of TRIS, 6.08 g of TAPS and 0.45 g of EDTA in 500 ml of water. Into this buffer 20 g of PVP (Mn=40,000) was added. The PVP was dissolved under slow stirring for approximately 4 hours. This produces a 50 mM Tris-TAPS buffer containing 4.0% PVP (w/v). At this concentration the PVP is present far below its entanglement threshold (see FIG. 1) in non-entangled form.

Filling Capillary Tube

A capillary tube in a capillary tube array in a MegaBACE® capillary electrophoresis system was filled with the separation media described above using a low pressure (100 psi). The capillaries used were coated with polyacrylamide.

Separation of Compounds

Electropherograms of separations of samples containing 20 oligonucleotides ranging from 11 to 30 bases is shown in FIGS. 2A and 2B. FIG. 2A shows a separation in a capillary filled with an entangled polyacrylamide matrix in 50 mM Tris-TAPS buffer. The sample was electrokinetically injected for 15 seconds at 10 kV. The separation was performed at 10 kV. The electropherogram shows that the peaks were poorly resolved. This is consistent with other separation systems in which a linear polyacrylamide entangled matrix was unable to resolve fragments of this size to single base separation. Instead, 2 base separation was common, resulting in overlap of bands differing by just one base. In contrast, the electropherogram of FIG. 2B shows the intensity peaks detected from a non-entangled PVP separation matrix. In this separation non-entangled PVP as used to separate the samples. 4.0% PVP (Mr=40,000) was used in 50 mM Tris-TAPS buffer. The samples were injected for 5 seconds at 15 kV. The samples were then separated at 15 kV using the MegaBACE® capillary electrophoresis system. The results from FIG. 2B show that the peaks are much more distinct, allowing identification of all peaks from the 11 to 30 base fragments. The order in which the samples pass the detection location is revered from FIG. 2A to FIG. 2B. When PVP is used as a separation matrix, as in FIG. 2B, the larger fragments migrate more quickly than the smaller fragments. The opposite is true for entangled matrices, such as the one used in FIG. 2A.

In FIG. 2, the microchannel containing linear polyacrylamide was run at a lower voltage than the capillary containing PVP. When linear polyacrylamide or similar viscous sieving matrices are used as the separation media, increasing voltage may result in band broadening. This limits the voltage that may be used in the separation, placing a constraint on the speed of separation. In contrast, when using a low viscosity PVP as the separation media, the greatest source of band broadening is longitudinal diffusion. If the time the sample stays in the microchannel is shortened, diffusion is reduced. The PVP allows the use of higher voltages, resulting in more rapid migration, less diffusion, and sharper detection peaks. In this example, most of the fragments from 11–30 bases, with each fragment differing by a single base, could be separated using the MegaBACE with a high resolution in less than 20 minutes.

When standard fluorescent dyes are used, 30 base pair fragments appear to be the upper limit for single base resolution. If the fragments are known to be each separated by at least 2 bases in length, it should be possible to separate fragment sets containing fragments longer than 30 bases and still achieve detectable resolution. Since not all applications require a 1 bp resolution, this matrix can be applied for separation of fragments up to 100 bp. In addition if energy transfer dyes are used, single base resolution of fragments longer than 30 bases should be possible. Energy transfer dyes are more hydrophobic than the dyes used in this example. This would increase retention times of this dye and result in a wider separation window.

FIGS. 3A and 3B illustrate further advantages achieved through the use of the higher voltages for separation. As shown in FIG. 3A, increasing the voltage from 6 kV to 12 kV results in a narrower peak. At the higher voltages, the compounds separated spend less time in the capillary, are less subject to diffusion and thus produce a narrower peak. This enhances the ability to detect fragments that differ by a single base. FIG. 3B illustrates the improvement in peak efficiency produced by separations at higher voltages. In this graph, for all three sizes of DNA fragments, 11 base pairs, 20 base pairs and 30 base pairs, show increased separation efficiency as the voltage is increased.

We claim:

1. A method for electrophoretic separation of a mixture of oligonucleotide fragments, wherein said mixture contains at least two fragments of different lengths and said lengths are between 0 and 100 bases the steps of the method comprising;
   a) filling at least one microchannel with a separation media, said separation media including non-entangled polyvinylpyrrolidone using pressure loading at a pressure not greater than 100 psi;
   b) injecting the mixture of oligonucleotide fragments into a first end of said microchannel;
   c) applying through said separation media an electrophoretic current sufficient to cause said oligonucleotide fragments to migrate through said separation media;
   wherein an interaction between said separation media and said fragments retards the migration of said fragments, wherein smaller fragments are retarded to a greater degree than larger fragments;
   d) detecting separated oligonucleotide fragments at a detection location in said microchannel removed from said injection end of said microchannel.

2. The method of claim 1, wherein said step of detecting separated compounds is effected by detection of laser induced fluorescence as fragments migrate past a detection window.

3. The method of claim 1, wherein said step of detecting separated compounds is effected by mass spectrometry.

4. The method of claim 1, wherein said at least one microchannel is part of an array of microchannels, wherein steps a through d are effected in each microchannel in said array of microchannels.

5. The method of claim 4, wherein said array of microchannels is a capillary tube array.

6. The method of claim 4, wherein said array of microchannels is a plurality of microchannels defined by a separation substrate.

7. The method of claim 1, wherein steps b and c are repeated at least twice, wherein following each injection step, an electrophoretic current is applied for an interval such that each mixture of fragments is detectably separated from any other mixture of fragments when each mixture of fragments migrates past the detection location.

8. The method of claim 1, wherein the step of filling the microchannel includes treating an interior surface of said microchannel to inhibit electroosmosis.

9. The method of claim 8, wherein treating the microchannel to inhibit electroosmosis includes adding a dynamic coating to the separation media.

10. The method of claim 8, wherein treating the microchannel to inhibit electroosmosis includes coating the interior surface of the capillary with a static coating.

11. The method of claim 8, wherein treating the microchannel to inhibit electroosmosis includes covalent modification of the interior surface of the microchannel.

12. The method of claim 1, wherein said separation media includes a denaturing agent.

13. The method of claim 1, wherein said separation media includes an intercalating agent.

14. The method of claim 1, wherein the lengths of said fragments is between 11–30 bases.

15. The method of claim 1, wherein said separation media is free of an entangled, sieving matrix.

16. The method of claim 1, wherein said separation media includes non-entangled polyvinylpyrrolidone added to a known separation media.

* * * * *